United States Patent [19]
Dirmi et al.

[11] Patent Number: 5,491,069
[45] Date of Patent: Feb. 13, 1996

[54] BIOMARKERS OF CELL SENESCENCE

[75] Inventors: Goberdhan P. Dirmi, Simli U.P., Ind.; Judith Campisi, Berkeley, Calif.; Monica Peacocke, Newton, Mass.

[73] Assignee: The Regents of the University of California, Oakland, Calif.

[21] Appl. No.: 198,436

[22] Filed: Feb. 18, 1994

[51] Int. Cl.$^6$ ............... C12Q 1/34; C12N 9/38; G01N 21/75; G01N 21/76
[52] U.S. Cl. ............... 435/18; 435/4; 435/29; 435/195; 435/207; 436/164; 436/172
[58] Field of Search ............... 435/4, 18, 29, 435/195, 207, 968; 436/164, 172

[56] References Cited

U.S. PATENT DOCUMENTS

| | | | |
|---|---|---|---|
| 4,683,195 | 7/1987 | Mullis | 435/6 |
| 4,683,202 | 7/1987 | Mullis | 435/91.2 |
| 5,302,706 | 4/1994 | Smith | 536/23.1 |

OTHER PUBLICATIONS

Jongkind et al. "Cell Softing & Microchemistry of Cultured Human Fibroblasts: Applications in Genetics & Aging Research" Cytometry 5(2) 182–187 1984.

Leroy et al. "The Effect of Aging on Acid B–D–Galactosidase In Human Liver Cell Lines" Biol. Cell 47(2) 235–238 1983.

Aizawa and Kurimoto, "Age–related cell surface changes in human diploid fibroblasts revealed by lectin–mediated red blood cell adsorption assay: a lectin survey," Mechanisms of Ageing and Development, 11:245–252 (1979).

Bosmann et al., "Loss of a critical neutral protease in ageing WI–38 cells," Nature, 261:499–501 (1976).

Busse et al., "Senescence–induced alteration in cell surface carbohydrates correlated using proton NMR spectroscopy and a lectin–based affinity–binding assay," Biochimica et Biophysica Acta, 984:183–187 (1989).

Goldstein, "Replicative senescence: The human fibroblast comes of age," Science, 249:1129–1133 (1990).

Hayflick, L., "The limited in vitro lifetime of human diploid cell strains," Experimental Cell Research, 37:614 (1965).

Hayflick and Moorhead, "The serial cultivation of human diploid cell strains," Experimental Cell Research, 25:585 (1961).

Klunder and Hulser, "B–galactosidase activity in transfected Ltk⁻ cells is differentially regulated in monolayer and in spheroid cultures," Experimental Cell Research, 207:155–162 (1993).

McCormick and Campisi, "Cellular aging and senescence," Current Opinion in Cell Biology, 3:230–234 (1991).

Ning et al., "Tumor suppression by chromosome 11 is not due to cellular senescence," Experimental Cell Research, 192:220–226 (1991).

Ning et al., "Genetic analysis of indefinite division in human cells: Evidence for a cell senescence–related gene(s) on human chromosome 4," Proc. Natl. Acad. Sci., 88:5635–5639 (1991).

Ning and Pereira–Smith, "Molecular genetic approaches to the study of cellular senescence," Mutation Research, 256:303–310 (1991).

O'Brien et al., "Suppression of tumor growth by senescence in virally transformed human fibroblasts," Proc. Natl. Acad. Sci., 83:8659–8663 (1986).

Peacocke and Campisi, "Cellular senescence: A reflection of normal growth control, differentiation, or aging?" Journal of Cellular Biochemistry, 45:147–155 (1991).

Pereira–Smith et al., "Immortal phenotype of the HeLa variant D98 is recessive in hybrids formed with normal human fibroblasts," Journal of Cellular Physiology, 142:222–225 (1990).

(List continued on next page.)

*Primary Examiner*—Michael G. Wityshyn
*Assistant Examiner*—Nancy J. Degen
*Attorney, Agent, or Firm*—Medlen & Carroll

[57] ABSTRACT

The present invention provides a biomarker system for the in vivo and in vitro assessment of cell senescence. In the method of the present invention, β-galactosidase activity is utilized as a means by which cell senescence may be assessed either in in vitro cell cultures or in vivo.

14 Claims, 1 Drawing Sheet

OTHER PUBLICATIONS

Pereira–Smith and Smith, "Genetic analysis of indefinite division in human cells: Identification of four complementation groups," Proc. Natl. Acad. Sci., 85:6042–6046 (1988).

Pereira–Smith and Smith, "Evidence for the recessive nature of cellular immortality," Science, 221:964–966 (1983).

Porter, et al., "Novel monoclonal antibodies identify antigenic determinants unique to cellular senescence." Journal of Cellular Physiology, 142:425–433 (1990).

Rose, et al., "Expression of c–fos and AP–1 activity in senescent human fibroblasts is not sufficient for DNA synthesis," Journal of Cell Biology, 119:1045–1411 (1992).

Schulte–Hermann et al., "Promotion of spontaneous preneoplastic cells in rat liver as a possible explanation of tumor production by nonmutagenic compounds," Cancer Research 43:839–844 (1983).

Seshadri and Campisi, "Repression of c–fos Transcription and an altered genetic program in senescent human fibroblasts," Science, 247:205–209 (1990).

Smith and Pereira–Smith, "Genetic and molecular studies of cellular immortalization," Advances in Cancer Research, 54:63–77 (1990).

Smith and Pereira–Smith, "Altered gene expression during cellular aging," Genome 31:386–389 (1989).

Smith and Pereira–Smith, "Further studies on the genetic and biochemical basis of cellular senescence," Experimental Genetics, 24:372–381 (1989).

Spiering, et al., "Correlation between complementation group for immortality and DNA synthesis inhibitors," Experimental Cell Research, 195:541–545 (1991).

Stanulis–Praeger, "Cellular senescence revisited: A review," Mechanisms of Ageing and Development, 38:1–48 (1987).

Sugawara et al., "Induction of cellular senescence in immortalized cells by human chromosome 1," Science 24:707–710 (1990).

West, et al., "Replicative senescence of human skin fibroblasts correlates with a loss of regulations and overexpression of collagenase activity," Experimental Cell Research, 184:138–147 (1989).

Wright, et al., "Reversible cellular senescence: Implications for immortalization of normal human diploid fibroblasts," Molecular and Cellular Biology, 9:3088–3092 (1989).

Yang and Homsby, "Dissociation of senescence–associated changes in differentiated gene expression and replicative senescence i ncultured adrenocortical cells," J. Cell Sci., 94:757 (1989).

BIOMARKERS OF CELL SENESCENCE

GOVERNMENT RIGHTS

This invention was made with Government support under Contract No. DE-AC03-76SF00098 between the U.S. Department of Energy and the University of California for the operation of Lawrence Berkeley laboratory. The Government has certain rights in this invention.

FIELD OF THE INVENTION

The present invention relates to cellular senescence, in particular, reagents and methods to differentiate senescent cells from other cells in vitro and in vivo.

BACKGROUND OF THE INVENTION

A fundamental characteristic of normal cells is their limited ability to proliferate in culture. While differentiated cells may have potential in vivo proliferative capacity, once placed in culture, the cells typically undergo an initial milotic period that is invariably followed by a gradual decline in cell division. This decrease in cell division is virtually irreversible and complete. Cell death usually occurs, although the cells may remain viable for long time periods. This progression of events from actively dividing cells to nondividing cells is termed "cellular senescence" or the "finite lifespan phenotype."

Only some primitive stem cells (e.g., the inner cell mass of early embryos) may have the potential for unlimited proliferation in culture. In vivo, differentiation serves to restrict stem cell proliferation during organismal development. There are several lines of evidence which indicate that cells senesce in vivo, due to the finite lifespan phenotype.

Cell senescence was first systematically described approximately 30 years ago, in such publications as L. Hayflick, "The limited in vitro lifetime of human diploid cell strains," Exp. Cell Res., 37:614 (1965); and Hayflick and Moorhead, "The serial cultivation of human diploid cell strains," Exp. Cell. Res., 25:585 (1961). Despite the fact that cell senescence was first described long ago, our molecular understanding of cell senescence is still incomplete. However, the limited in vivo data available indicate that senescence is not merely an artefact of cell culture. Rather, it appears to be genetically-based. Largely due to the lack of an animal model or useful in vivo methods to permit its study in humans and other animals, cell cultures are the most common method used to study the processes associated with cell senescence.

Various agents, such as carcinogens (e.g., chemicals, viruses and oncogenes) are capable of immortalizing normal cells. By itself, immortality is insufficient for neoplastic transformation. However, most immortal cells have an increased tendency for spontaneous, carcinogen-induced, or oncogene-induced neoplastic progression. Thus, escape from senescence may be a pre-neoplastic change that results in the predisposition to neoplastic conversion. Based on these observations, it has been hypothesized that cellular senescence is a major mechanism involved in tumor suppression. O'Brien et al., "Suppression of tumor growth by senescence in virally transformed human fibroblasts," Proc. Natl. Acad. Sci., 83:8659 (1986).

Of the various theories used to explain senescence, there is much evidence to indicate that senescence is a genetically programmed process. Based on cell fusion studies (e.g., microcell fusions to produce hybrid cells), it has been determined that at least four genetic complementation groups are associated with immortality. Smith and Pereira-Smith, "Genetic and molecular studies of cellular immortalization," Adv. Cancer Res., 54:63 (1990); Pereira-Smith and Smith, "Genetic analysis of indefinite division in human cells: Identification of four complementation groups," Proc. Natl. Acad. Sci., 85:6042 (1988); Smith and Pereira-Smith, "Altered gene expression during cellular aging," Genome 31:386 (1989); and Pereira-Smith and Smith, "Evidence for the recessive nature of cellular immortality" Science 221:964 (1983).

Individual chromosomes have been associated with the induction of senescence. For example, human chromosome 1 was shown to induce senescence in such cells as an immortal hamster cell line, while chromosome 11 had no effect on the growth of the cells [Sugawara et al., "Induction of cellular senescence in immortalized cells by human chromosome 1," Science 24:707 (1990); Ning et al., "Tumor suppression by chromosome 11 is not due to cellular senescence, Exp. Cell Res., 192:220 (1991); and Ning and Pereira-Smith, "Molecular genetic approaches to the study of cellular senescence," Mut. Res., 256:303 (1991).] Human chromosome 4 was found to limit the proliferative lifespan of three immortal human tumor cell lines [Ning et al., "Genetic analysis of indefinite division in human cells: Evidence for a cell senescence-related gene(s) on human chromosome 4," Proc. Natl. Acad. Sci., 88:5635 (1991)]. Thus, at least two different human chromosomes have been shown to reverse the immortal phenotype following their introduction into established cell lines. See also, Wright et al., "Reversible cellular senescence: Implications for immortalization of normal human diploid fibroblasts," Mol. Cell. Biol., 9:3088 (1989).

Furthermore, there is evidence that oncogenes can immortalize human cells, usually by encoding multifunctional nuclear proteins for which there is neither an identified single structural cellular homologue, nor an identified single function cellular homologue. These proteins bind and may serve to inactivate at least two tumor suppressor gene products (e.g., the cellular proteins p53 and the retinoblastoma susceptibility gene product [Rb])[McCormick and Campisi, "Cellular aging and senescence," Current Opinion in Cell Biology 3:230 (1991)]. These and other genetic experiments indicate that senescence is dominant over immortality [see e.g., Pereira-Smith et al., "Immortal phenotype of the HeLa variant D98 is recessive in hybrids formed with normal human fibroblasts," J. Cell. Physiol., 142:222 (1990)]. Indeed, it is hypothesized that multiple genes might be lost or inactivated during cellular escape from senescence.

Recent investigations indicate that the cessation of cell division is just one facet of a very complex senescent phenotype. For example, changes in cell function are also associated with cell senescence. Further complexity is added by studies on cultured well-differentiated epithelial cells which suggest that changes in differentiated functions of cells and the arrest of cell proliferation can be dissociated from each other [Yang and Homsby, "Dissociation of senescence-associated changes in differentiated gene expression and replicative senescence in cultured adrenocortical cells," J. Cell Sci., 94:757 (1989)]. Thus, in order to gain a full understanding of the nature and significance of cell senescence, an understanding of both types of changes (i.e., those that result in growth inhibition and those that alter differentiated functions) must be gained.

Attempts to gain this understanding are hampered by the conditions and testing methods in current use. There are relatively few assays that can distinguish normal and senescent cells. For example, unlike normal cells, cultured senescent cells do not proliferate in response to mitogens. In addition, there is no method to distinguish senescent cells from quiescent, terminally differentiated or physiologically compromised cells in tissues without culturing the cells that migrate out of tissue explants. These studies require cumbersome, labor and time-intensive methods which are not suited to rapid and cost-effective assessment of the status of cells in vivo or in vitro. Furthermore, these assays are not definitive nor predictive in terms of the actual physiological characteristics of the cells.

Thus, the majority of the present assay systems rely on assessment of gene expression, such as methods involving incorporation of radiolabelled thymidine or thymidine analogues. In these assays, senescent cells do not incorporate the radiolabelled compound. However, quiescent cells also do not incorporate these compounds. Therefore, this type of assay is only useful under carefully controlled culture conditions. Importantly, most of these methods are toxic to cells, limiting their value if continuing cell growth is desired or required for further study. In addition, these toxic compounds present concerns regarding the cost and safety of their disposal. Furthermore, they cannot be used to identify senescent cells present in heterogeneous cell cultures.

What is need is a rapid, convenient, easy-to-use, means to identify senescent cells present in a mixed cell population. Such a method should ideally permit the researcher to differentiate senescent from quiescent, terminally differentiated or physiologically compromised cells.

SUMMARY OF THE INVENTION

The present invention relates to cellular senescence, in particular, reagents and methods to differentiate senescent cells from other cells in vitro and in vivo.

In one embodiment, the present invention provides a method for a method for assaying senescence in cells, comprising the steps of: 1) exposing said cells to a quantity of substrate for β-galactosidase sufficient for detection of β-galactosidase activity, wherein said exposing is conducted at a pH in the range of approximately 5.5 to 6.5; and 2) detecting said β-galactosidase activity. In a preferred embodiment, the assaying is conducted at approximately pH 6.0.

It is contemplated that the method of the present invention will involve assaying of cells in vitro. In one embodiment, the cells are in vitro cell cultures. In another preferred embodiment, the assayed cells are isolated from a sample obtained from a patient. In a preferred embodiment, the sample is selected from the group consisting of biopsy and surgical samples.

In one embodiment of the present invention, the substrate is labelled. In one embodiment, the label is selected from the group comprising fluorescent compounds, chromogens, dyes, radioactive compounds, and enzymes. It is contemplated that the β-galactosidase substrate 5-bromo-4-chloro-3-indolyl-β-D-galactopyranoside will be used as a label. In another preferred embodiment, the labelled substrate is fluorescein digalactopyranoside. It is contemplated that the labelled substrate be fluorescein di-β-Dgalactopyranoside will be used.

In an alternative embodiment, the method of the present invention further comprises: step 3) separating cells expressing said β-galactosidase activity from cells not expressing said β-galactosidase activity. In a further embodiment, the present invention also includes: step 4) culturing said cells expressing said β-galactosidase activity. In an additional embodiment, the present invention includes: step 5) culturing said cells not expressing said β-galactosidase activity.

In an alternative embodiment, the present invention comprises a method for assaying senescence in cells, comprising the steps of: 1) exposing cells to a quantity of substrate for β-galactosidase sufficient for detection of β-galactosidase activity, wherein exposing is conducted at a pH in the range of approximately 5.5 to 6.5; 2) exposing the cells to a counterstain for a time sufficient to permit staining of cellular components; and 3) detecting β-galactosidase activity. In a preferred embodiment, the assaying is conducted at approximately pH 6.0.

In one preferred embodiment, the cells are isolated from a sample obtained from a patient. In one embodiment, the sample is selected from the group consisting of biopsy and surgical samples. In a particularly preferred embodiment, the counterstain is eosin.

In additional alternative embodiment, the present invention comprises a method for assaying senescence in cells, comprising the steps of: 1) exposing cells to a quantity of fluorogenic substrate for β-galactosidase sufficient for detection of β-galactosidase activity, wherein the exposing is conducted at a pH in the approximate range of 5.5 to 6.5; 2) detecting β-galactosidase activity; and 3) separating cells expressing β-galactosidase activity from cells which do not express β-galactosidase activity. In a preferred embodiment, the method further comprises: step 4) culturing cells which express β-galactosidase activity.

GENERAL DESCRIPTION OF THE INVENTION

Figure 1:
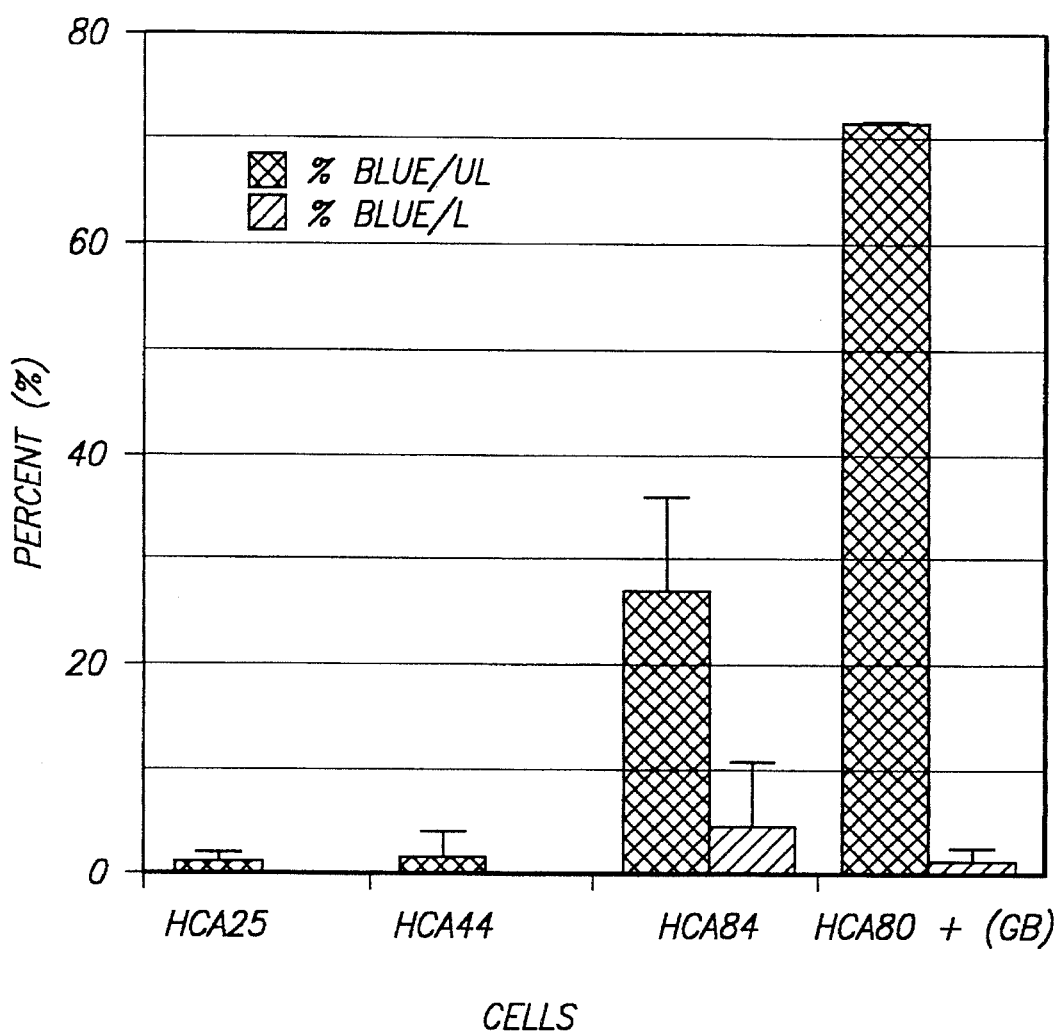
FIG. 1 shows a graph of the percent of stained and/or labelled cells for four different HCA cell passages.

The present invention relates to cellular senescence, in particular, reagents and methods to differentiate senescent cells from other, non-senescent cells in vitro and in vivo. The invention permits the researcher to distinguish senescent from quiescent, terminallydifferentiated and physiologically-compromised cells. Specifically, the present invention is based on the surprising observation that senescent cells may be distinguished from presenescent cells by histochemical staining for β-galactosidase activity. Under the assay conditions of the present invention, β-galactosidase activity is easily detectable in senescent cells, but undetectable in quiescent, immortal or tumor cells.

The assay of the present invention provides a rapid and inexpensive method to identify individual senescent cells in cultures comprised of a mixture of quiescent or nonquiescent pre-senescent and/or immortal, and senescent cells. In contrast to the prior art, the method of the present invention does not rely on DNA synthesis measurements for detection of senescent cells (e.g., thymidine uptake). The present invention provides an assay method which differentiates senescent from other cells without the use of radioactivity or time-consuming and expensive immunodetection methods presently in use (e.g., detection of bromodeoxyuridine).

Importantly, it is contemplated that the method of the present invention will permit rapid identification of the senescent phenotype in uncharacterized cell cultures. Moreover, the method of the present invention also provides a means to identify differentiated functions which have been altered by senescence.

The present invention contemplates that the method of the present invention can be combined with other techniques to assess (1) the degree to which benign or malignant tumors or transformed cells have escaped senescence, (2) the regenerative capacity of tissues before surgical procedures are conducted, and (3) the extent to which proliferative stimuli of mechanical, chemical, viral, hormonal or other origins have exhausted the proliferative capacity of a tissue or cell type.

The present invention permits study of the genes responsible for inducing cell senescence in various cell cultures. It is contemplated therefore, that the present invention will be useful for distinguishing various cell types, including but not limited to, such cells as normal human fibroblasts, endothelial cells, epithelial cells, immortal, tumorigenic human fibrosarcoma, carcinoma, and retinoblastoma cell lines. Specifically, the present invention provides a screening method useful to identify and test the effects of the genes which control and/or participate in senescence. Chromosome fragments or cDNAs that induce senescence are distinguishable from chromosome fragments or cDNAs that act to arrest cell growth due to toxicity, abnormal or ectopic expression or induction of quiescence or terminal differentiation.

It is contemplated that these functions and/or genes will be targets for biological and/or pharmacological (e.g., pharmaceutical) intervention. Indeed, the present invention provides a method to screen for direct and/or side effects of biological and/or pharmacological compounds, in particular those which lead to induction of senescence or premature senescence in normal cells, as well as induction of senescence in immortal and/or tumor cells. It is contemplated that these compounds will be useful in treatment of hyperproliferative, hypoproliferative and/or age-associated disorders. It is also contemplated that the present invention will be useful in studies to reverse and/or delay senescence in normal cells and/or tissues.

Although it is not intended to limit the method, it is contemplated that the present invention will provide targeted therapies by linking the β-galactosidase substrate with a compound that is cytotoxic or affects the cell's biochemistry, physiology or genome.

It is further contemplated that the method of the present invention will provide targeted therapies designed to facilitate tissue and organ transplantations. For example, it is contemplated that the method of the present invention will serve to identify senescent cells in tissues to be transplanted. Following this identification, the senescent cells may be eliminated or the senescent characteristic reversed, if so desired. The method of the present invention also provides a means by which autologous treatment of cells may be achieved. For example, it is possible to identify senescent cells in such samples as blood. Following this identification and isolation, the sample may be treated to remove these cells and the remaining cells reintroduced into the patient.

The method also provides a means for pharmacological or biological elimination of cells with detrimental functions. For example, by targeting senescent cells, the method of the present invention provides a basis for pharmacological or biological elimination of senescent cells, or their modification so as to alter detrimental characteristics, and/or reverse the potential effects of senescence.

The method of the present invention is also intended for use in screening mutant alleles that induce premature senescence in normal cells. Applications of this invention thereby include, but are not limited to study of the genes responsible for premature aging syndromes (e.g., Werner's syndrome).

In one embodiment, the invention utilizes fluorogenic β-galactosidase substrates. This permits the use of flow cytometry using such commercially available instruments as fluorescence activated cell sorters (FACS) if desired. The use of FACS spacers facilitates the quantitation and characterization of senescent cells present in heterogenous cell populations. In addition to the studies of fleshly isolated and cultured cells, the present invention contemplates a method for identification and isolation of cells (e.g., by FACS) from humans or other animals to produce viable cultures from tissues or fluid samples (e.g., blood) with particular cell characteristics. These cells are then available for testing for senescence. This is in contrast to other methods which compromise cell viability. Thus, the present invention represents a significant advantage for studies which involve further characterization of cells. Also, because cells may be sorted by FACS into viable senescent and non-senescent groups, characteristics of cells present in either or both groups are available for further study, including evaluation of biologicals and/or pharmaceuticals which enrich cell populations for either senescent or non-senescent cells. It is further contemplated that these cells be targeted for reintroduction into living organisms.

It is not intended that the invention be limited by the source of the cells studied (e.g., muscle, heart, brain, etc.). For example, the present invention provides a rapid, convenient and inexpensive means to identify seriescent cells in tissue biopsy material. It is also contemplated that the assay will also be used to assess the replicative history of tissues, thereby providing a method for evaluation of the physiological, in contrast to the chronological age of the tissue. This information provides useful information for diagnostic and prognostic purposes, especially in cases involving a hyperproliferative or hypoproliferative response, or chronic stimulation of cell proliferation.

The present invention also contemplates a rapid, convenient, inexpensive diagnostic and/or prognostic assay for evaluation of diseases associated with high cell turnover rates. It also contemplates an assay for assessment of the extent to which the proliferative capacity of cells has been exhausted due to local or environmental damage, viral, bacterial or eukaryotic pathogens, or pathological conditions of genetic and/or acquired origins. The present invention also contemplates a rapid, convenient, inexpensive assay for the in vivo assessment in humans, other animals, and/or animal models for the anti-neoplastic, anti-aging and/or proliferation-modulating compounds or treatment regimens.

DETAILED DESCRIPTION OF THE INVENTION

The present invention is predicated in part on the discovery that senescent cells express optimal β-galactosidase activity at pH 6.0. This is in contrast to the pH optimum of 4.0 for lysosomal β-galactosidase activity ubiquitous among eukaryotes, as well as the pH optimum of 7.5 documented for bacterial β-galactosidase activity.

In one embodiment of the method of the present invention, cells to be assayed for this distinctive β-galactosidase activity are fixed in situ (e.g., using formaldehyde and glutaraldehyde diluted in PBS). The fixed cells are then exposed to an artificial β-galactosidase substrate (e.g., X-gal), and incubated at 37° C. in the presence of sodium and magnesium chloride, potassium ferrocyanide, potassium ferricyanide, and citrate/phosphate buffer to maintain the pH at 6.0. A blue precipitate forms in situ over the cells which express an X-gal cleaving activity.

Senescent cells cleave X-gal at pH 6, while this cleaving activity is not detectable at pH 6 in pre-senescent cells whether they are growing or quiescent, immortal or tumor cells. The assay requires less than 15 minutes to prepare and although staining is maximal after overnight incubation (12–16 hours), it is usually detectable within 2 hours.

In another embodiment of the present invention, cells to be assayed for this distinctive β-galactosidase activity are fixed and exposed to a fluorogenic β-galactosidase (FDG) substrate, including but not limited to such substrates as fluorescein di-β-D-galactopyranoside (e.g., $C_{12}FDG$). In this embodiment, the action of the enzyme on the substrate typically results in the release of a fluorescent product (e.g., fluorescein).

The present invention contemplates a method for studying tumor cells, as screening of various skin tumors (basal and squamous cell carcinomas) for β-galactosidase activity using the present invention revealed that some, but not all tumors tested exhibit areas of positive staining.

It is contemplated that after staining for β-galactosidase activity, chromosome fragments or cDNA's introduced into cells can be recovered. The polymerase chain reaction (PCR) disclosed in U.S. Pat. Nos. 4,683,195 and 4,683,202 to Mullis, hereby incorporated by reference, is contemplated for recovery and characterization of DNA from any number of cells. It is contemplated that PCR will be useful for screening chromosome fragments or cDNA's (i.e., genes) for senescence-inducing activity. It is further contemplated that these genes be anti-proliferative or tumor-suppressive in activity.

Importantly, the present invention contemplates the use of an animal model (including, but not limited to, rodents [e.g., rats], as well as other animals) for evaluation of biological and pharmaceutical compounds with anti-tumor, anti-aging, and/or proliferationmodulating properties. For example, using the present invention revealed that senescent rat embryo fibroblasts stain strongly positive in the present assay. In contrast, cells in early passages (i.e., pre-senescent cells) do not stain.

Definitions

As used herein, the term "senescent" is used in reference to cells which are incapable of further cell division. Commonly used criteria to establish cell senescence include, but are not limited to such factors as cellular enlargement and flattening, cessation of proliferation as measured by the failure to increase the number of cells in culture over a two-week period, failure to subculture or form colonies at clonal density, and lack of significant incorporation of [$^3$H] thymidine. Although senescent cells remain viable for long time periods, they cannot be stimulated to enter the S phase of the cell cycle by any combination of growth factors or physiological milogens.

Senescent cells may remain viable for long time periods (many months), during which RNA and protein are synthesized. Thus, in a strict sense, cell senescence is not the equivalent of programmed cell death. Nonetheless, "senescence" is commonly used in reference to the stages of the cell lifespan which ultimately result in cell death.

As used herein, the term "proliferation" and "growth" are used interchangeably to indicate cell division.

As used herein, the term "quiescent" is used in reference to cells which are not proliferating, but which can be stimulated to enter the S stage in the cell cycle when appropriate growth factors are present.

As used herein the term "terminally differentiated" is used in reference to cells and tissues which have reached their final stages of development. For example, terminally differentiated cells are those which have attained the specialized characteristics associated with a particular cell type.

As used herein, the term "immortal phenotype" refers to cells and cell lines which have essentially infinite lifespans. Typically, immortal cell lines (e.g. continuous cell lines) are those which have been transformed and lack such characteristics commonly associated with normal cells as contact inhibition, an increased growth rate, etc.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein the term "S phase," or "S stage" refer to the phase of the cell growth cycle in which DNA synthesis occurs. The remaining stages of the cell cycle are indicated as "M phase" in reference to milosis, "$G_1$," in reference to the growth phase occurring after mitosis but before the S phase, and "$G_2$," used in reference to a second growth phase which occurs after DNA synthesis.

As used herein, the term "stain" and "dye" refer to any color which results is used as an indicator for the presence of a particular compound. These terms also refer to any compound which imparts color to a structure or compound. It is contemplated that this color production be the result of enzymatic or other activity. For example, the reaction of β-galactosidase on such substrates as X-gal results in the staining of cells which express this enzymatic activity.

As used herein, the term "β-galactosidase substrate" refers to any natural or artificial (e.g., synthetic) compound upon which β-galactosidase may act. This term encompasses the various commercially available β-galactosidase substrates, including, but not limited to: 5-bromo- 4-chloro-3-indolyl-β-D-galactoside; 5-bromo-4-chloro-3-indolyl-β-D-galactopyranoside (i.e., X-gal, available from numerous chemical suppliers, such as Sigma, Research Organics, and other companies); 5-bromoindolyl-β-D-galactopyranoside; ortho-nitrophenyl-β-D-galactopyranoside (i.e., ONPG); and fluorescein di-β-D-galactopyranosides (FDG), as well as carboxyfluorescein compounds (e.g., $C_{12}FDG$) available from Molecular Probes. It is further not intended that the present invention be limited to the color produced. For example, some compounds such as X-gal produce a blue color upon reaction with figalactosidase, while others such as ONPG, produce a yellow color. In addition, other stains and dyes are contemplated for use in the present invention as indicators of β-galactosidase activity.

As used herein, the term "label" refers to any compound which serves as an indicator of the presence of a particular substance. Fluorogenic, chromogenic, enzymatic or radioactive compounds as well as any other compound which acts as an indicator may serve as labels. Thus, "label" also encompasses some compounds which are "stains" or "dyes."

As used herein, the term "counterstain" refers to any staining material (including, but not limited to dyes), which when exposed to cells will impart color to cell components. This term includes, but is not limited to such commonly used stains as eosin (e.g., eosin Y), commercially available from numerous chemical suppliers (e.g., Sigma) as well as most large scientific distributors (e.g., Fisher Scientific, Pittsburgh, PA).

As used herein, the phrase "escape from senescence" refers to the reversion of immortal cell lines with introduced chromosomes associated with senescence, to their original immortal phenotype. This term also refers to any cells, whether or not they are cell lines, previously associated with the senescent phenotype, which are immortal.

EXPERIMENTAL

The following examples serve to illustrate certain preferred embodiments and aspects of the present invention and are not to be construed as limiting the scope thereof.

A large variety of cell lines at various passage levels, and primary cultures were used in the development of the present invention. Some of the cell lines were used in the following examples, while others were used in experiments which are not described below. Table 1 includes the sources and most of the cell lines used in the development of the present invention. As shown in this Table, many of the cell lines were provided through the generous courtesy of various individuals and companies.

TABLE 1

Cell Lines and Sources

| Patrick Hensler, of Baylor College of Medicine, Houston, TX | |
| --- | --- |
| EJ (bladder carcinoma) | EJ + 1 (EJ cells with introduced human chromosome 1) |
| | EJ + 4 (EJ cells with introduced human chromosome 4) |
| HeLa (cervical cancer) | HeLa + 4 (HeLa cells with introduced chromosome 4) |
| T98G (glioblastoma) | T98G + 4 (T98G cells with introduced human chromosome 4) |
| TE85 (osteosarcoma) | TE85 + 1 (TE85 cells with introduced human chromosome 1) |
| CMV-Mj-HEL (human lung epithelial fibroblasts infected with cytomegalovirus) | CMV-Mj-HEL + 1 (CMV-Mj-HEL cells with introduced human chromosome 1) |
| Olivia Smith, of Baylor College of Medicine, Houston, TX | |
| HCA2 (human diploid fibroblasts; also referred to as HCA) | |
| George Martin, of the University of Washington, Seattle, WA | |
| Normal human fibroblasts | Primary human skin fibroblasts obtained from Werner's Syndrome patients and age-matched controls |
| Aging Cell Repository of the National Institute of Aging | |
| WI-38 | WI-38 cells transformed with SV40 |
| American Type Culture Collection (ATCC) | |
| Saos-2 (human osteogenic sarcoma) (ATCC HTB 85) | HeLa (ATCC CCL 2) |
| TE85 (ATCC CRL 1543) | HT1080 (human fibrosarcoma)(ATCC HT1080) |
| HTB 9(human bladder carcinoma) (ATCC HTB 9) | UTOS (human osteogenic sarcoma)(ATTC HTB 96) |

In the experimental disclosure which follows, the following abbreviations apply: eq (equivalents); M (Molar); μM (micromolar); N (Normal); mol (moles); mmol (millimoles); μmol (micromoles); nmol (nanomoles); gm or g (grams); mg (milligrams); μg (micrograms); ng (nanograms); L (liters); ml (milliliters); μl (microliters); cm (centimeters); mm (millimeters); μm (micrometers); nm (nanometers); hr (hour); min. (minutes); sec. (seconds); °C. (degrees Centigrade); FACS (fluorescence-activated cell sorter); NaCl (sodium chloride); $MgCl_2$ (magnesium chloride); DME (Dulbecco's Modified Eagle's medium); FCS (fetal calf serum); PBS (phosphate buffered saline, pH 7.5); citric acid/phosphate buffer (0.1M citric acid solution combined with sodium phosphate solution, pH 6.0); citric acid solution (2.1 g/100 ml citric acid monohydrate; 0.1M); sodium phosphate solution (2.84 g/100 ml sodium dibasic phosphate ($Na_2HPO_4$) or 3.56 g/100 ml sodium dibasic phosphate dihydrate ($Na_2HPO_4.H_2O$); X-gal (5-bromo-4-chloro-3-indolyl-β-D-galactopyranoside); DAPI (4,6-diamidino-2-phenylindole); FDG (fluorescein di-β-D-galactopyranoside); $C_{12}FDG$ (fluorescein di-β-D-galactopyranoside with a 12-carbon chain); Research Organics (Research Organics, Inc., Cleveland, Ohio); Sigma (Sigma Chemical Co., St. Louis, MO.); Molecular Probes (Molecular Probes, Eugene, OR); ATCC (American Type Culture Collection, Rockville, Md.).

Primary cultures were obtained from human umbilical endothelial cells (HUVEC), human ovarian surface epithelial cells, and normal human mammary epithelial cells. In addition, human ovarian surface epithelial cells infected with SV40 were also used.

EXAMPLE 1

In this example, human diploid fibroblasts (HCA cells of various passage levels) were stained by the method of the present invention and observed for the expression of β-galactosidase activity.

First, the medium present on cultured cells were removed, the cells washed twice in PBS, and fixed in 2–3 ml of fixing solution comprised of a 2 % formaldehyde and 0.2% glutaraldehyde in PBS. The cells were incubated at room temperature for 5 minutes, then washed twice with PBS. The cells were then incubated at 37° C. (without $CO_2$) for 1 to 16 hours in 2–3 ml of a solution comprising potassium ferricyanide (5 mM), potassium ferrocyanide (5 mM), $MgCl_2$ (2 mM), X-gal (1 mg/ml), in citric/phosphate buffer. Following this incubation period, the cell samples were observed in order to detect the presence of blue cells, indicating that X-gal had been cleaved (e.g., a positive test result). In this experiment, senescent cells, but not other cells were stained blue due to the action of β-galactosidase on the substrate.

EXAMPLE 2

In this experiment the effects of buffer aM pH were tested in the β-galactosidase assay. Mid and late passage HCA cells were prepared as described in Example 1, with the exception that some cultures were tested with PBS at pH 7.5, while others were tested with the citrate/phosphate buffer at pH 6.0 of Example 1.

In this example, no reaction was observed at pH 7.5, nor pH 6.0 for the low passage cells. For the late passage cells, 80–90% of the cells stained strongly positive at pH 6.0, while there was no reaction at pH 7.5.

EXAMPLE 3

In this example, the effects of pH on β-galactosidase activity were further studied, using citrate phosphate, sodium phosphate and PBS. In this example, senescent HCA and young HCA cells were tested in pH conditions ranging from 3 to 8, and incubated for 3–4 hours as well as overnight. The following tables show the results observed for the senescent and young cells respectively. In these tables, the intensity of staining due to cleavage of Xgal is indicated on a scale of "−" (indicating no staining) to 4+ (indicating very strongly positive staining).

TABLE 2

Results Observed With Senescent HCA Cells
After 3–4 Hours of Incubation

| Buffer | pH | Percent of Cells Stained (Approximate) | Intensity of Staining |
|---|---|---|---|
| Citrate Phosphate | 3.0 | 50% | 2+ |
| | 4.0 | 98–100% | 4+ |
| | 5.0 | 20–30% | 3+ |
| | 6.0 | 20–30% | 3+ |
| Sodium Phosphate | 7.0 | 1% | ± |
| | 8.0 | 0% | — |

TABLE 3

Results Observed With Senescent HCA Cells
After Overnight Incubation

| Buffer | pH | Percent of Cells Stained (Approximate) | Intensity of Staining |
|---|---|---|---|
| Citrate Phosphate | 3.0 | 50% | 3+ |
| | 4.0 | 100% | 4+ |
| | 5.0 | 80–90% | 3+ |
| | 6.0 | 90–100% | 3+ |
| Sodium Phosphate | 7.0 | 1% | ± |
| | 8.0 | 0% | — |

TABLE 4

Results Observed With Young HCA Cells
After 3–4 Hours of Incubation

| Buffer | pH | Percent of Cells Stained (Approximate) | Intensity of Staining |
|---|---|---|---|
| Citrate Phosphate | 3.0 | 50–60% | 3+ |
| | 4.0 | 50–60% | 4+ |
| | 5.0 | 10–20% | 3+ |
| | 6.0 | 0% | — |
| Sodium Phosphate | 7.0 | 0% | — |
| | 8.0 | 0% | — |

TABLE 5

Results Observed With Young HCA Cells
After Overnight Incubation

| Buffer | pH | Percent of Cells Stained (Approximate) | Intensity of Staining |
|---|---|---|---|
| Citrate Phosphate | 3.0 | 50%–60% | 3+ |
| | 4.0 | 100% | 4+ |
| | 5.0 | 50% | 3+ |
| | 6.0 | 1% | ± |
| Sodium Phosphate | 7.0 | 0% | — |
| | 8.0 | 0% | — |

As shown in the above tables, following overnight incubation, approximately 100 % of both the senescent and young cells stained strongly at pH 4. The results are even more remarkable at pH 6.0, with 90 % of the senescent cells staining strongly positive, but less than 1% of the young cells staining.

As expected, both the young and old cells expressed lysosomal β-galactosidase activity at pH 3–4, the optimal pH for this particular enzyme. However, the senescent cells also contained significant β-galactosidase activity at pH 6.0, while the young cells did not. This experiment demonstrates the utility of this invention in distinguishing between senescent and young cells.

EXAMPLE 4

In this example, the effect of serum deprivation on young cells was investigated. It is known that serum-deprived cells do not readily synthesize DNA. Thus, this experiment was designed to determine whether cells which are not growing produce positive β-galactosidase activity results at pH 6.0.

In this experiment, young HCA cells were prepared and tested as described in Example 1, with the exception being that no FCS was used in their growth medium. As a control, the assay was conducted both at pH 4.0 and pH 6.0. Cells were observed at various intervals of incubation in serum-free medium, ranging from 48 to 168 hours. The following table shows the results obtained in these assays after overnight staining. As in the tables from the previous Example, the intensity is indicated within a range of "−" to "4 +."

TABLE 6

Results for Young, Serum-Deprived HCA Cells

| Time of Exposure to Serum-Free Medium | Staining Intensity Percent of Positive Cells at pH 4.0 | Staining Intensity* and Percent of Positive Cells at pH 6.0 |
|---|---|---|
| 48 Hours | 3+ (100%) | <5 (only in very dense places) |
| 72 Hours | 3+ (100%) | <5% |
| 96 Hours | 3+ (100%) | <5% |
| 144 Hours | 3+ (100%) | <5% |
| 168 Hours | 3+ (100%) | <5% |

*For these cells, there essentially was no staining; the intensity was negligible.

Based on these results, serum-deprivation appears to have little effect on the lysosomal β-galactosidase activity at pH 4.0. In addition, serum-deprivation appears to have no effect on the expression of β-galactosidase activity in young cells at pH 6.0.

EXAMPLE 5

In this experiment, the fluorescence of human diploid fibroblasts was measured alone and with $Cl_2FDG$. The FDG test is useful to detect the presence of β-galactosidase, as FDG is cleaved by this enzyme to fluorescein monogalactoside, and then to the fluorescent compound fluorescein.

Early passage, mid-passage and late passage HCA cells were grown on microscope coverslips at varying cell densities, in 2 ml of DME with 10% FCS. Fresh 10% DME with FCS containing 50 μM $C_{12}FDG$ was added to test coverslips, while fresh 10% DME with FCS was added to the control coverslips. The cultures were incubated for 1 hr at 37° C., and then rinsed once with PBS. The coverslips were mounted on microscope slides and viewed with a standard fluorescence microscope fitted with standard filters suitable for use with fluorescein, at various magnifications (e.g., 1000×).

Fluorescein-stained cells (i.e., green colored) were observed in senescent cell populations. No fluorescence was observed with early passage cultures. Based on these observations, the use of FACS was suggested, as fluorescein dyes are useful for FACS staining and the filter band width may be manipulated to produce the optimal degree of staining. In this manner, contrast may be enhanced.

EXAMPLE 6

In this experiment, various cell types cultured on microscope coverslips, including TE85, TE85+1, CMV-Mj-HEL+1, and HCA2 cells at early passage (27 passages), mid passage (41 passages) and late passage (80 passages) were allowed to grow overnight and tested using the protocol of Example 5. Fresh 10% FCS-DME was added to the control cultures; fresh 10% FCS with 50 μM $C_{12}FDG$ (Molecular Probes) was added to the test cultures. The cells were allowed to incubate for an hour at 37° C.. One set of test cells was fixed in a 100 % methanol for one minute. The cells were then treated with DAPI for one minute. The test and control cells were washed five times in PBS and rinsed in PBS for 30 minutes. All of the coverslips were then mounted on microscope slides and observed as described above.

Some auto fluorescence was observed, especially in older cells. In this example, it was recognized that the microscope probably had a wider band width filter than that available with FACS. Thus, it was hypothesized that autofluorescence could be cut down in order to observe the pH 6, $C_{12}FDG$-dependent, β-galactosidase fluorescence by use of FACS.

EXAMPLE 7

In this experiment the thymidine uptake of senescent and non-senescent cells was studied in conjunction with β-galactosidase assays using X-gal. HCA2 cells of early (passage 25; designated HCA25), medium (passage 44; designated HCA44), late (passage 84; designated HCA84), and very late (passage 80+; designated HCA80+[GB]) were tested.

Multiple sets of cells cultured on microscope coverslips (indicated by "test number" in the accompanying table) were incubated with tritiated (10 μCurie/ml) thymidine ($^3$[H]-TDR) for 48 hours. The cells were then fixed and stained for β-galactosidase activity as in Example 1. At the conclusion of staining, the cells were washed with PBS and fixed again with methanol, dried, and exposed to a photographic emulsion to permit observation of thymidine uptake. The results are shown in the following table. As used in this table, "labelled" refers to cells that took up the thymidine, "unlabelled" refers to cells that did not take up the thymidine, "stained/labelled" refers to cells that were positive for β-galactosidase activity and took up the tritiated thymidine, and "stained/unlabelled" refers to cells that were positive for β-galactosidase activity, but did not take up the thymidine.

TABLE 7

| | | Number of Cells: | | | |
|---|---|---|---|---|---|
| Cell Lines | Test Number | Labelled | Un-labelled | Stained/Labelled | Stained/Unlabelled |
| HCA25 | 1 | 91 | 3 | 0 | 1 (very light) |
| | 2 | 103 | 2 | 0 | 0 |
| | 3 | 97 | 3 | 0 | 0 |
| | 4 | 113 | 2 | 0 (2 very light) | 1 (light) |
| HCA44 | 1 | 22 | 11 | 0 | 0 |

TABLE 7-continued

| | | Number of Cells: | | | |
|---|---|---|---|---|---|
| Cell Lines | Test Number | Labelled | Un-labelled | Stained/ Labelled | Stained/ Unlabelled |
| | 2 | 17 | 1 (4 w/light label) | 0 | 1 |
| | 3 | 35 | 3 | 0 | 1 |
| | 4 | 28 | 8 | 0 | 0 |
| | 5 | 20 | 4 | 0 | 0 |
| | 6 | 16 | 8 | 0 (1–2 very light) | 0 (2 very light) |
| HCA84 | 1 | 6 | 2 | 0 | 2 very, very light |
| | 2 | 4 | 3 | 0 | 2 |
| | 3 | 3 | 4 | 1 light blue | 1 very blue |
| | 4 | 9 | 5 | 2 light blue | 5 |
| | 5 | 5 | 6 | 0 | 3 bright blue |
| | 6 | 2 | 5 | 0 | 1 bright blue |
| | 7 | 4 | 1 | 0 | 1 bright blue |
| | 8 | 3 | 2 | 0 | 3 bright blue + 1 light blue |
| | 9 | 3 | 7 | 1 | |

TABLE 8

| | Cumulative Totals | | | | |
|---|---|---|---|---|---|
| Cells | Labelled (%) | Un-labelled (%) | Stained/ Labelled (%) | Stained/ Unlabelled (%) | Total Number of Cells (%) |
| HCA25 (early passage) | 404 (97) | 10 (3) | 0 (0) | 2 (0.5) | 414 |
| HCA44 (mid-passage) | 138 (80) | 35 (20) | 1 (0.5) | 4 (2) | 173 |
| HCA84 (late passage) | 39 (53) | 35 (47) | 4 (5) | 21 (28) | 74 |
| HCA80 + (GB) (very late passage) | 3 (3) | 88 (97) | 1 (1) | 65 (71) | 91 |

TABLE 9

| | Quantitation of Data | | | |
|---|---|---|---|---|
| Cells | Number | Percent of Cells Labelled | Percent of Cells Stained and Labelled | Percent of Cells Stained and Unlabelled |
| HCA25 | 1 | 96.8 | 0 | 1.1 |
| | 2 | 98.1 | 0 | 0 |
| | 3 | 97.0 | 0 | 0 |
| | 4 | 98.3 | 0 | 0.9 |
| Average: | | 97.5 ± 2.3 | 0 | 1.0 ± 0.8 |
| HCA44 | 1 | 66.7 | 0 | 0 |
| | 2 | 94.4 | 0 | 5.5 |
| | 3 | 92.1 | 0 | 2.6 |
| | 4 | 77.8 | 0 | 0 |
| | 5 | 83.3 | 0 | 0 |
| | 6 | 66.7 | 0 | 0 |
| Average: | | 80.2 ± 12.0 | 0 | 1.4 ± 2.3 |
| HCA84 | 1 | 75.0 | 0 | 25 |
| | 2 | 57.1 | 0 | 28.6 |

TABLE 9-continued

Quantitation of Data

| Cells | Number | Percent of Cells Labelled | Percent of Cells Stained and Labelled | Percent of Cells Stained and Unlabelled |
|---|---|---|---|---|
| | 3 | 42.8 | 14.3 | 14.3 |
| | 4 | 64.3 | 14.3 | 35.7 |
| | 5 | 45.5 | 0 | 27.3 |
| | 6 | 28.6 | 0 | 42.9 |
| | 7 | 80.0 | 0 | 20.0 |
| | 8 | 60.0 | 0 | 20.0 |
| | 9 | 30.0 | 10.0 | 30.0 |
| Average: | | 53.7 ± 18.3 | 4.3 ± 6.5 | 27.1 ± 8.7 |
| HCA80 + | 1 | 6.5 | 2.2 | 71.7 |
| (GB) | 2 | 0.0 | 0.0 | 71.1 |
| Average: | | 3.3 ± 3.3 | 1.1 ± 1.1 | 71.4 ± 0.3 |

Blue cells were observed, both unlabelled and labelled. As demonstrated by the very high passage number (HCA 80+ [GB]), with increasing numbers of passages, the staining became darker. For the oldest cells, there were none labelled and all were blue, ranging from a bright blue to an almost opaque color.

FIG. 1 illustrates the label/stain data obtained with HCA cells. In this Figure, the solid bars indicate the percentages of cells which stained for β-galactosidase activity, but were unlabelled (i.e., negative for DNA synthesis). The hatched bars indicate the percentages of cells which stained for β-galactosidase activity, and were also labelled (i.e., positive for DNA synthesis).

EXAMPLE 8

In this example, immortal cell lines were tested for β-galactosidase activity using the same protocol as described in Example 7.

For this experiment, TE85 clones were plated at cell densities of approximately $2 \times 10^4$ and labelled with radioactive thymidine for 48 hours. Then, the cells were stained with x-gal for 16 hours, and incubated with assay emulsion for 48 hours.

In 95–97 % of the cells that were labelled with radioactivity, none were stained blue. Thus, in this experiment no β-galactosidase activity was observed in the immortal cells.

EXAMPLE 9

In this experiment, a parental cell line (TE85) was tested in conjunction with cells with introduced human chromosome 1 or 2 (TE85+1, and TE85+2).

Multiple plates of cells were prepared and subjected to the same protocol described in Example 7, in which the β-galactosidase and DNA synthesis activities were measured concurrently.

As expected, there was no evidence of chromosome 2 acting to produce senescence, as no blue staining was observed. However, there also was no blue staining observed with the cells that contained chromosome 1. Concurrently, it was also observed that the particular clone used in this experiment had escaped senescence and regained its immortal phenotype, an observation which was consistent with the absence of β-galactosidase activity at pH 6.

EXAMPLE 10

In this experiment, CMV-Mj-HEL (the parent cell line) and CMV-Mj-HEL+1 cells (i.e., microcell hybrids containing human chromosome 1) were tested for β-galactosidase activity. This cell line contains human chromosome 1, which has been associated with the development of senescence. CMV-Mj-HEL cells are normally immortal, but are reported to develop the senescent phenotype upon introduction of human chromosome 1.

Four sets of each cell type were grown at cell densities of approximately 110 cells/cm$^2$ and approximately 550 cells/cm$^2$. The cells were then stained for β-galactosidase activity and treated to determine tritiated thymidine uptake as in Example 7.

In this experiment, for the CMV-Mj-HEL+1 cells, three groups of cells were observed: (1) cells that stained bright blue, and were not labelled; (2) cells that stained light blue, and were labelled; and (3) cells that did not stain blue, but were labelled. As shown in the following table. A total of 310 total cells was observed, 70 of which were in group 1 (22%), 52 were in group 2 (17%), and 188 were in group 3 (61%). Of these 310 cells, 240 (78%) were labelled, indicating that DNA synthesis was occurring in the cells.

TABLE 10

Results for CMV-Mj-HEL + 1 Cells

| GROUP | NUMBER OF CELLS | PERCENTAGE |
|---|---|---|
| 1 | 70 | 22% |
| 2 | 52 | 17% |
| 3 | 188 | 61% |
| NUMBER OF CELLS: | 310 | |

Thus, these results indicated that in a population of cells which contain human chromosome 1, there are subpopulations of cells which are senescent (group 1), in addition to growing cells (group 3), and cells which may be in a transition stage from a growing to senescent phenotype (group 2).

It is interesting that in a follow-up experiment using low density cell cultures (60 to 120 cells per slide), a majority of the CMV-Mj-HEL+1 cells had escaped senescence and had regained their immortal phenotype.

EXAMPLE 11

In this example, low density cultures (60 to 120 cells per slide) of CMV-Mj-HEL+ 1 were tested for β-galactosidase and DNA synthesis activity using the protocol of Example 7. This experiment produced four groups of cells: (1) those with no stain and no label; (2) those which stained, but did not contain label; (3) those which were both stained and contained label; and (4) those with no stain, but were labelled.

In group 1, there were 26 cells, which were not senescent, but were not growing (i.e., they may have been in a quiescent state). There were 11 cells in group 2, indicating (i.e., to provide orientation as to the location within the cell layers collected in the biopsy material).

The following table shows the age, sex, H & E staining, tissue type tested, and the galactosidase activity for each patient tested in which a positive β-galactosidase test result was obtained.

TABLE 11

PATIENT RESULTS

| Patient | Age | Sex | Tissue | H & E | β-gal.* Activity | Positive Staining Location & Characteristics |
|---|---|---|---|---|---|---|
| 1 | 90 | M | Scalp | Yes | Yes | Pilosebaceous apparatus; Occasional cells in basal epidermal layer; Fibers of deep dermis; Occasional collagen fibers of the papillary & reticular dermis. |
| 2 | 75 | M | Scalp | Yes | Yes | Occasional single cells & focal areas of basal epidermal layer; superficial & deep collagen fibers; Glandular structures. |
| 3 | 73 | M | Temple | Yes | Yes | Pilosebaceous apparatus; Extensive, but patchy staining in basal epidermal areas; Superficial and deep collagen fibers; Glandular structures. |
| 4 | 81 | M | Neck | Yes | Yes | Pilosebaceous apparatus; Extensive, but patchy in basal epidermal areas (superficial and deep); Glandular structures. |
| 5 | 70 | F | Lip | Yes | Yes | Pilosebaceous apparatus; Extensive, but patchy in basal epidermal areas (superficial and deep); Glandular structures. |
| 6 | 81 | M | Lip | Yes | Yes | Pilosebaceous apparatus; Extensive, but patchy in basal epidermal areas; Superficial and deep glandular structures. |
| 7 | 76 | M | Arm | Yes | Yes | Pilosebaceous apparatus; Extensive, but patchy in basal epidermal areas (superficial and deep); Focal, patchy staining of collagen fibers; Glandular structures. |
| 8 | 73 | F | Nose | Yes | Yes | Pilosebaceous apparatus; Focal patchy staining of superficial and deep collagen fibers. |
| 9 | 69 | M | Temple | Yes | | Pilosebaceous apparatus; Focal patchy staining of superficial and deep collagen fibers. |
| 10 | 78 | F | Nose | Yes | | Pilosebaceous apparatus; Extensive, but patchy staining in superficial and deep basal epidermis. |
| 11 | 37 | F | Naso-labial Fold | Yes | | Pilosebaceous apparatus; Rare basal keratinocytes; Glandular structure. |
| 12 | 38 | F | Shoulder | Yes | | Pilosebaceous apparatus; Glandular structure. |
| 13 | 37 | F | Cheek | Yes | | Pilosebaceous apparatus; Glandular structure; One focal area of basal layer; one focal area of collagen fibers; Deep dermis; |
| 14 | 20 | F | Lip | Yes | | Pilosebaceous apparatus, Selected areas with tumor nests. |
| 15 | 39 | F | Shoulder | Yes | | Pilosebaceous apparatus. |
| 16 | 31 | M | Temple | Yes | | Pilosebaceous apparatus; Glandular structure; Patchy areas of basal epidermis. |
| 17 | 31 | F | Cheek | Yes | | Pilosebaceous apparatus |
| 18 | 38 | M | | Yes | | Pilosebaceous apparatus; Occasional staining in nests of tumor cells. |

*"β-gal." = β-galactosidase these cells were senescent. There were 9 cells in group 3, probably indicating cells which were in transition from non-senescence to senescence. Finally, there were 260 cells in group 4, indicating that the majority of the cells observed were not senescent, but were actively synthesizing DNA.

Based on these results, it appears that most of these cells plated at low densities were able escape senescence and regained their immortal phenotype.

EXAMPLE 12

In this example, tissue samples were obtained from 18 patients, and tested for galactosidase activity. Tissue biopsies obtained from these patients were quick frozen in liquid nitrogen until frozen and stored in a cryostat (−141 ° C.) until sectioning. After the samples were sliced into section of 4–5µ thick and mounted on microscope slides, the tissues were fixed and stained as described in Example 1. However, prior to observation, the samples were counterstained with eosin for 2 minutes. In addition to the sections of each sample stained by the method of Example 1, H & E staining was done using routine histochemical procedures in order to provide data regarding the orientation of the tissue section

EXAMPLE 13

In this example, cell samples from various patients were tested for the presence of senescent cells using the method of the present invention. Frozen tissue sections from surgical specimens from young (20–39 years of age) and old (69–90 years of age) patients were stained as described in Example 12.

Areas of positive staining were readily identified in the epidermis and the deep and superficial dermis in 10/10 of the elderly individuals. In contrast, the dermis of the 10/10 young people uniformly showed minimal staining, although isolated positive cells were found in the basal epidermal layers of three young people. Positive staining of sebum (i.e., oily secretions of sebaceous glands comprised of fat and epithelial debris) and eccrine (i.e., sweat) secretions was observed for all individuals tested.

The present invention is useful for assessment of surgical skin specimens. Areas of positive staining are readily observed in the dermis and/or basal epidermal layer of most older individuals. In contrast, the dermis and epidermis of younger individuals are largely negative for β-galactosidase activity, with only occasional positive staining. Terminally differentiated epidermal cells in both age groups were negative. Interestingly, eccrine secretions and hair follicles from both young and older individuals exhibit positive staining, which can be used as an internal positive control for the staining method. Sun-damaged skin, which undergoes a greater cell turnover than sun-protected skin, generally shows more cells and a greater level of activity than sun-protected skin, especially in older individuals.

From the above examples, it should be clear that the present invention allows for the rapid detection and differentiation of senescent cells from cells maintained in culture as well as cells freshly obtained from humans or other animals. The invention is easy to use and provides an assay system which permits separation of viable senescent cells from other cells.

What is claimed is:

1. A method for differentiating between senescent and young cells, comprising the steps of:
   a) providing:
      i) senescent cells,
      ii) young cells,
      iii) substrate for β-galactosidase activity; and
      iv) a buffer having a pH between approximately 5.5 and 6.5; and
   b) exposing said senescent cells and said young cells to said buffer containing said β-galactosidase substrate under conditions such that at least 90% of said senescent cells display β-galactosidase activity and said young cells display no significant β-galactosidase activity.

2. The method of claim 1, wherein said exposing further comprises incubating said senescent and said young cells for a period of time equal to between approximately 12 to 16 hours.

3. The method of claim 1, wherein said β-galactosidase substrate has a label.

4. The method of claim 3; wherein said label is selected from the group consisting of fluorescent compounds, chromogens, dyes, radioactive compounds, and enzymes.

5. The method of claim 1 further comprising step c) separating said senescent cells from said young cells.

6. The method of claim 5 further comprising step d) culturing said senescent cells.

7. The method of claim 6 further comprising step e) culturing said young cells.

8. A method for differentiating between senescent and young cells, comprising the steps of:
   a) providing:
      i) a tissue sample suspected of containing senescent cells and young cells;
      ii) a substrate for β-galactosidase activity; and
      iii) a buffer having a pH between approximately 5.5 and 6.5; and
   b) exposing said, tissue sample to said buffer containing said galactosidase substrate under conditions such that greater than 90% of said senescent cells display β-galactosidase activity and less than or equal to 1% of said young cells display β-galactosidase activity.

9. The method of claim 8, wherein said exposing further comprises incubating said senescent and said young cells for a period of time equal to between approximately 12 to 16 hours.

10. The method of claim 8, wherein said β-galactosidase substrate has a label.

11. The method of claim 10, wherein said label is selected from the group consisting of fluorescent compounds, chromogens, dyes, radioactive compounds, and enzymes.

12. The method of claim 8 further comprising step c) separating said senescent cells from said young cells.

13. The method of claim 12 further comprising step d) culturing said senescent cells.

14. The method of claim 13 further comprising step e) culturing said young cells.

* * * * *

UNITED STATES PATENT AND TRADEMARK OFFICE
CERTIFICATE OF CORRECTION

PATENT NO. : 5,491,069

DATED : February 13, 1996

INVENTOR(S) : Goberdhan P. Dimri et al.

Page 1 of 2

It is certified that error appears in the above-indentified patent and that said Letters Patent is hereby corrected as shown below:

ON THE COVER PAGE:

At "[75]", please delete "Dirmi" and insert --Dimri--.

under item [56] "OTHER PUBLICATIONS":

After "Jongkind et al." please delete "Softing" and insert --Sorting--.

After "Ning et al., 'Genetic analysis of indefinite division in human cells: Evidence for a cell senescence-related gene(s) on human chromosome 4,' Proc. Natl. Acad. Sci., 88:5635-5639 (1991)" please insert --Ning et al., "Tumor suppression by chromosome 11 is not due to cellular senescence," Experimental Cell Research, 192:220-226 (1991)--.

In column 1, line 23, please delete "milotic" and insert --mitotic--.
In column 2, line 20, please delete "cence," and insert --cence,"--.
In column 3, line 3, please delete "milogens" and insert --mitogens--.
In column 3, line 26, please delete "need" and insert --needed--.
In column 3, line 38, please delete "a method for".
In column 3, line 62, please delete "di-β-Dgalactopyranoside" and insert --di-β-D-galactopyranoside--.
In column 4, line 21, following "In" please insert --an--.
In column 4, line 33, please delete "BRIEF".
In column 4, line 43, please delete "terminallydifferentiated" and insert --terminally-differentiated--.
In column 4, line 46, please delete "presenescent" and insert --pre-senescent--.
In column 4, line 53, please delete "nonquies" and insert --non-quies--.
In column 6, line 7, please delete "fleshly" and insert --freshly--.
In column 6, line 27, please delete "seriescent" and insert --senescent--.

UNITED STATES PATENT AND TRADEMARK OFFICE
CERTIFICATE OF CORRECTION

PATENT NO. : 5,491,069

DATED : February 13, 1996

INVENTOR(S) : Goberdhan P. Dimri et al.

It is certified that error appears in the above-indentified patent and that said Letters Patent is hereby corrected as shown below:

In column 7, line 36, please delete "proliferationmodulating" and insert --proliferation-modulating--.

In column 7, line 55, please delete "milogens" and insert --mitogens--.

In column 7, line 48, please delete "figalactosidase" and insert --β-galactosidase--.

In column 10, line 55, please delete "were" and insert --was--.

In column 10, line 56, following cells, please insert --were--.

In column 11, line 8, please delete "aM" and insert --and--.

In column 13, line 25, please delete "Cl$_2$FDG' and insert --C$_{12}$FDG--.

In column 15, before "TABLE 8", please insert --The following tables provide the cumulative results for the cells.--.

In column 17, line 38, please delete "2x 10$^4$" and insert --2 x 10$^4$--.

In column 18, line 33, please delete "labelled. As" and insert --labelled as--.

In column 19, line 51, following "able", please insert --to--.

In column 21, line 36, please delete "claim 3;" and insert --claim 3,--.

In column 22, line 16, please delete "said," and insert --said--.

In column 22, line 17, please delete "galactosidase" and insert --β-galactosidase--.

Signed and Sealed this

Seventeenth Day of September, 1996

Attest:

BRUCE LEHMAN

Attesting Officer

Commissioner of Patents and Trademarks

UNITED STATES PATENT AND TRADEMARK OFFICE
CERTIFICATE OF CORRECTION

| | | |
|---|---|---|
| PATENT NO. | : 5,491,069 | Page 1 of 1 |
| APPLICATION NO. | : 08/198436 | |
| DATED | : February 13, 1996 | |
| INVENTOR(S) | : Dimri P. Goberdhan et al. | |

It is certified that error appears in the above-identified patent and that said Letters Patent is hereby corrected as shown below:

On the first page of the specification in the first paragraph entitled:

GOVERNMENT RIGHTS after "This invention was made with Government support", add

-- under Grant Nos. AG09909, AG11658, and AG09927 awarded by the National Institutes of Health and --

Signed and Sealed this
Fifteenth Day of February, 2011

David J. Kappos
*Director of the United States Patent and Trademark Office*